United States Patent

Baudin et al.

[11] Patent Number: 4,457,862
[45] Date of Patent: Jul. 3, 1984

[54] ODORANT SUBSTANCES

[75] Inventors: Josiane Baudin, Annemasse, France; Hans U. Gonzenbach, Geneva, Switzerland

[73] Assignee: Givaudan Corporation, Clifton, N.J.

[21] Appl. No.: 441,597

[22] PCT Filed: Feb. 25, 1982

[86] PCT No.: PCT/CH82/00029
§ 371 Date: Nov. 9, 1982
§ 102(e) Date: Nov. 9, 1982

[87] PCT Pub. No.: WO82/03216
PCT Pub. Date: Sep. 30, 1982

[30] Foreign Application Priority Data

Mar. 13, 1981 [CH] Switzerland ............... 1718/81
Feb. 11, 1982 [CH] Switzerland ............... 841/82

[51] Int. Cl.³ ............... C07C 49/537; A61K 7/46
[52] U.S. Cl. ............... 252/522 R; 568/376; 568/377; 568/379; 568/378
[58] Field of Search ............... 252/522 R; 568/376, 568/378, 379, 377

[56] References Cited

U.S. PATENT DOCUMENTS 3,578,686  5/1971  Tuliar et al. ............... 568/376
3,845,133 10/1974  Cohen ............... 568/379

Primary Examiner—James H. Reamer
Attorney, Agent, or Firm—Robert F. Tavares

[57] ABSTRACT

New odoriferous compounds, particularly the compounds having the following formula:

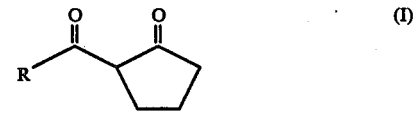

wherein R is an aliphatic residue having the formula

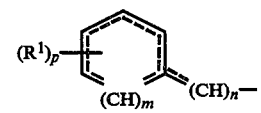

wherein $R^1$ is a $C_{1-4}$ alkyl, $C_{1-4}$ alkylidene or $C_{2-4}$ alkenyl, the sum of the carbon atoms being in those residues from 2 to 5, m and n being equal to zero or 1, p being 1, 2 or 3 and the dotted lines representing one or two optional double bonds. The invention also relates to a method for the preparation of new di-ketones I: as well as the use of I as odoriferous compounds in odoriferous compositions, which are characterized by a certain proportion of compounds having the formula I.

11 Claims, No Drawings

ODORANT SUBSTANCES

The invention is concerned with novel odorant substances. These are compounds of the formula

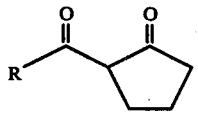

wherein R signifies an aliphatic group of the formula

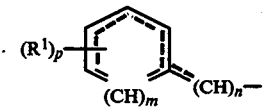

in which $R^1$ is $C_{1-4}$-alkyl, $C_{1-4}$-alkylidene or $C_{2-4}$-alkenyl and the sum of the carbon atoms in these groups is 2-5, m and n are 0 or 1, p is 1, 2 or 3 and the dotted lines represent one or two optional double bonds.

The alkyl, alkenyl or alkylidene groups denoted by $R^1$ can be straight-chain or branched-chain. Examples of alkyl groups are methyl, ethyl, propyl, isopropyl, n-butyl, sec.-butyl and tert.-butyl. Vinyl, propenyl, isopropenyl and butenyl are examples of alkenyl groups. Examples of alkylidene groups are methylidene, ethylidene, propylidene, isopropylidene and butylidene.

$R^1$ is preferably methyl. p is preferably 3. When p is 2 or 3 the groups $R^1$ can be the same or different. m is preferably the same as n; m and n both being 1 are especially preferred.

R preferably represents one of the following groups:

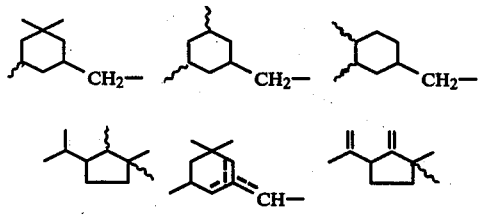

The first of these groups is particularly preferred.

Formula I is also intended to embrace the stereoisomers which occur as a result of the asymmetric centres, the double-bond isomers and the corresponding enol forms of the diketones of formula I. The enol forms of the 1,3-diketones are:

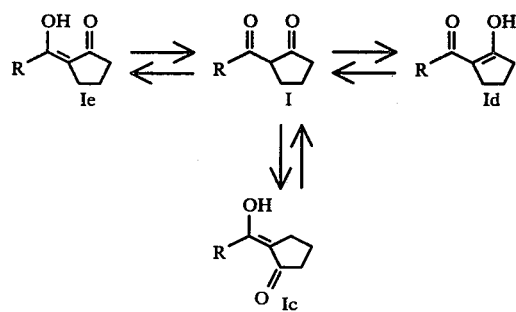

The present invention is also concerned with a process for the manufacture of the compounds of formula I.

This process comprises reacting an enamine of cyclopentanone with an acid halide of the formula

wherein R has the significance given earlier and X represents halogen.

As the acid halides there come into consideration especially the chloride, bromide and iodide, with the chloride being preferred.

The manufacture of the diketones of formula I can therefore be carried out according to the known methodology of enamine acylation; see, for example, G. Stork, A. Brizzolara, H. Landesmann, J. Szmuskovicz and R. Terrel in J. Amer. Chem. Soc. 85, 207 (1963).

As the enamine-former there can be used, for example, the following secondary amines:

Aliphatic secondary amines such as dialkylamines (e.g. diethylamine) or cyclic secondary amines such as, for example, morpholine, piperidine or pyrrolidine. Morpholine is preferred.

The reaction of the enamine with the halide of formula II is conveniently carried out in a solvent and with the exclusion of air and moisture. Suitable solvents are anhydrous solvents such as, for example, methylene chloride, chloroform, dioxan, benzene, toluene, dimethyl formamide etc; methylene chloride and chloroform are preferred.

The molar ratio of enamine to halide is conveniently approximately 1:1, but the enamine can also be used in excess (e.g. in a two-fold amount or even more). However, the addition of any amine (e.g. triethylamine) can replace the excess of the enamine necessary to neutralize the acid formed.

The reaction is conveniently carried out at a temperature between 0° C. and the reflux temperature of the reaction mixture, preferably at about 40° C. For example, the mixture is left for several hours at this temperature. Thereupon, the mixture is cooled, conveniently to room temperature, and then an acid (e.g. hydrochloric acid) is added thereto. The amine-cleavage can then be achieved by renewed heating (e.g. at reflux temperature).

The isolation of the reaction product can be carried out according to methods known per se. For example, the reaction product is taken up in an organic solvent and the organic solution is washed firstly with dilute hydrochloric acid such as a 10% HCl solution. After washing neutral and drying, the crude product can be purified by usual methods such as, for example, adsorption chromatography and/or distillation.

The compounds of formula I have particular organoleptic properties, on the basis of which they are excellently suited as odorant substances.

The invention is accordingly also concerned with the use of the compounds of formula I as odorant substances.

The compounds of formula I possess, in particular, woody-animal like olfactory notes; they are distinguished, in particular, by high olfactory intensity associated with extraordinary diffusion and exceptional tenacity.

When used in low concentrations, the compounds of formula I intensify the olfactory notes of odorant substance compositions, especially of woody or animal-like compositions or bases, and confer to these warmth and radiance.

Examples of such compositions are compositions with cedarwood, sandalwood and patchouli notes as well as costus and castoreum notes.

The compounds of formula I are also excellently suited for the modification of leather notes and chypre notes, not only of the feminine but also of the masculine direction.

The compounds of formula I combine with numerous known odorant substance ingredients of natural or synthetic origin, whereby the range of the natural ingredients can embrace not only readily-volatile but also semi-volatile and slightly-volatile components, and the range of the synthetic ingredients can embrace representative from practically all classes of substances, as will be evident from the following compilation:

Natural products such as ambergris, bergamotte oil, castoreum and its substitute, acetylated cedarwood oil (e.g. Vertofix TM IFF or Cedartone TM Givaudan), tree moss, tarragon oil, pine-needle oil, galbanum oil, geranium oil, jasmine absolute and its substitute, lavandin oil, lavender oil, mandarin oil, orange oil, osmanthus absolute and its substitute, patchouli oil, petitgrain oil Paraguay, sandalwood oil, vetiver oil, wormwood oil and ylang-ylang oil;

alcohols such as borneol, cedrol, citronellol, eugenol, geraniol, cis-3-hexenol, linalool, 3-methyl-5-(2',2',3'-trimethyl-cyclopent-3'-en-1'-yl)-pentan-2-ol (Sandalore ® Givaudan), phenylpropyl alcohol, vetivenol and cinnamic alcohol;

aldehydes such as p-tert.butyl-α-methyl-dihydro-cinnamaldehyde (e.g. Lilial ® Givaudan), citral, decanal, 3,5-dimethyl-cyclohex-3-ene-carboxaldehyde, heliotropin, α-hexylcinnamaldehyde, hydroxycitronellal, methylnonylacetaldehyde, 4-[4-methyl-3-pentenyl]-cyclohex-3-ene-1-aldehyde (e.g. Myraldine ® Givaudan), syringa aldehyde and vanillin;

ketones such as acetylcedrene, α-ionone, camphor, menthone, p-methylacetophenone and methyl ionone;

esters such as ethyl 3-ethyl-1,1-dimethyl-cyclohex-3-ene-2-carboxylate (Givescone TM Givaudan), benzyl acetate, benzyl salicylate, bornyl acetate, p-tert.butylcyclohexyl acetate, cedryl acetate, cis-3-hexenyl acetate, linalyl acetate, 4-[4-methyl-3-pentenyl]-cyclohex-3-en-1-yl-carbinyl acetate (e.g. Myraldyl Acetate TM Givaudan), methyl dihydrojasmonate and styrallyl acetate;

lactones such as γ-undecalactone and coumarin;

various further components often used in perfumery such as acetaldehyde-propylphenyl-ethyl acetal, methyl 1-methyl-cyclododecyl ether (e.g. Madrox TM Givaudan), musk compounds [musk ambrette, musk ketone, 12-oxa-hexadecanolide (e.g. Musk 174 ®  Naarden), 1,1-dimethyl-4-acetyl-6-tert.-butylindane, indole)] and skatole.

The compounds of formula I can be used in wide limits which, for example, can extend in compositions from 0.01% (detergents) to 10% (alcoholic solutions). It will, however, be appreciated that these values are not limiting values, since the experienced perfumer can also achieve effects with lower concentrations or even only traces of the compounds or can synthesize novel complexes with higher concentrations. The preferred concentrations vary between 0.5% and 1.5%. The compositions produced with the compounds of formula I can be used for all kinds of perfumed consumer goods (Eau de Cologne, eau de toilette, essences, lotions, creams, shampoos, soaps, salves, powder, deodorants, detergents, tobacco etc).

The compounds of formula I can therefore be used in the production of odorant substance compositions and, as will be evident from the foregoing compilation, a wide range of known odorant substances can be used. In the production of such compositions, the known odorant substances specified earlier can be used according to methods known to the perfumer such as, for example, according to W. A. Poucher, Perfumes, Cosmetics and Soaps 2, 7th Edition, Chapman and Hall, London, 1974.

EXAMPLE 1

Dihydroisophorone 2.2 kg of isophorone and 5 g of 5% palladium-on-carbon catalyst are added to a 3 liter autoclave which is fitted with heating means, cooling means and a stirrer. A hydrogen pressure of 8–10 atmospheres is now generated and the mixture is slowly warmed to 30°–35° C. Since the hydrogenation is exothermic, provision is made by cooling that a temperature of 50° C. is not exceeded. After completion of the hydrogen uptake (temperature drop), the catalyst is filtered off. There are thus obtained 2.2 kg of crude dihydroisophorone, which is uniform according to gas chromatography and which is used directly.

$n_D^{20} = 1.4455$. Yield: quantitative.

Ethyl 1-hydroxy-3,3,5-trimethyl-cyclohexylacetate 300 ml of absolute ether, 150 ml of dry benzene and 170 g of magnesium shavings are added to a 6 liter flask which is fitted with a stirrer, thermometer, dropping funnel and reflux condenser. Now, there is introduced dropwise a mixture of 1.100 kg of dihydroisophorone and 960 g of ethyl chloroacetate dissolved in 1.200 l of ether and 600 ml of benzene. (If the reaction does not begin during the addition of the first 200 ml and warming at slight reflux does not begin spontaneously, then a few small crystals of iodine are added). The beginning of the reaction is recognizable by turbidity and heat-evolution. The addition of the reagents is continued in such a manner that the mixture boils only moderately, the addition being completed within 1¼ hours. Thereafter, the mixture is held at reflux temperature for a further 3½ hours and, after cooling, added to 2.5 kg of ice and 1.2 l of concentrated hydrochloric acid. The organic phase is separated and washed with water (containing 1% concentrated hydrochloric acid), with water and several times more with 10% sodium carbonate solution. After evaporating the solvent in vacuo, there remain behind 1.69 kg of crude product which are distilled. The main fraction (1.250 kg) is washed with 10% sodium carbonate solution and again distilled (100° C./3 mm Hg). There are thus obtained 1.046 kg of ethyl 1-hydroxy-3,3,5-trimethyl-cyclohexylacetate.

$n_D^{20} = 1.4580$. Yield: 62%.

Ethyl 3,3,5-trimethyl-(1 or 6)-(cyclohexenyl or cyclohexylidene)acetate 1.040 kg of ethyl 1-hydroxy-3,3,5-trimethyl-cyclohexylacetate, 35 g of potassium hydrogen sulphate and 300 ml of toluene are heated while stirring vigorously in a 2 liter flask which is fitted with a stirrer, thermometer and reflux condenser with a water-separator. 78 ml of water are separated within 4 hours at an internal temperature of 140°–150° C. The mixture is thereupon cooled, washed with 10% sodium carbonate solution and the toluene is evaporated in vacuo. There are obtained 990 g of crude product which are distilled and yield 880 g of an isomer mixture (GC: 3 peaks).

$n_D^{20} = 1.4560-1.4640$. Yield: 92%.

3,5-Dimethyl-cyclohexanone 128 g of 3,5-dimethyl-cyclohexanol and 500 ml of benzene are added to a round flask which is fitted with a stirrer, thermometer, dropping funnel and reflux condenser. While stirring and cooling there is now slowly added dropwise thereto a mixture of 119 g of sodium dichromate, 500 ml of water, 162 ml of concentrated sulphuric acid and 50 ml of glacial acetic acid. Thereby the temperature should not exceed +10° C. The mixture is stirred at this temperature for a further 3 hours and then the organic phase is separated. The aqueous phase is diluted with 130 ml of water and extracted with benzene. The combined organic phases are washed neutral and concentrated. The residue is distilled over a Widmer column and gives 102.7 g of 3,5-dimethyl-cyclohexanone.

B.p.: 55° C./6 mm Hg, $n_D^{20} = 1.4432$. Yield: 82%.

3,4-Dimethyl-cyclohexanone

Corresponding oxidation of 3,4-dimethyl-cyclohexanol yields 3,4-dimethyl-cyclohexanone.

B.p.: 66° C./11 mm Hg.

Ethyl 3,5-dimethyl-cyclohexylideneacetate 85 g of dry toluene are added to a round flask which is fitted with a stirrer, thermometer, dropping funnel and reflux condenser. Under a nitrogen atmosphere there are now introduced 17.2 g of sodium in small portions and the mixture is heated to boiling. After dissolution of the sodium (after about 3 hours), the mixture is cooled to 20° C. and there is slowly added dropwise thereto (during about 1½ hours) a mixture of 219 g of ethyl diethylphosphonoacetate, 95 g of 3,5-dimethyl-cyclohexanone and 220 g of dry toluene. The temperature is held between 25° and 30° C. The mixture is stirred at this temperature for a further 2 days and thereupon poured on to 400 g of ice, extracted with toluene, washed neutral and concentrated. The residue is distilled over a Widmer column and thus yields 110 g of ethyl 3,5-dimethyl-cyclohexylideneacetate.

B.p.: 58° C./0.04 mm Hg; $n_D^{20} = 1.4720$. Yield: 75%.

Ethyl 3,4-dimethyl-cyclohexylideneacetate

When 3,4-dimethyl-cyclohexanone is subjected to the foregoing Wittig-Horner conditions there is obtained ethyl 3,4-dimethyl-cyclohexylideneacetate.

B.p.: 56° C./0.08 mm Hg; $n_D^{20} = 1.4769$.

Ethyl 2-sec.butyl-cyclohexylideneacetate

By the analogous reaction of 2-sec.butyl-cyclohexanone there is obtained ethyl 2-sec.butyl-cyclohexylideneacetate.

B.p.: 92° C./0.3 mm Hg; $n_D^{20} = 1.4839$.

Ethyl 3,3,5-trimethyl-cyclohexylacetate 875 g of ethyl 3,3,5-trimethyl-(1 or 6)-(cyclohexenyl or cyclohexylidene)acetate, 5 g of 5% palladium-on-carbon and 25 g of sodium carbonate are added to a 3 liter autoclave which is fitted with heating means, cooling means and a stirrer. A hydrogen pressure of 20 atmospheres is generated and the mixture is heated to 75° C. The hydrogenation proceeds rapidly and exothermically and the mixture must therefore be cooled in order that a temperature of 100° C. is not exceeded. After cooling, the mixture is filtered. There are obtained in quantitative yield 875 g of a diastereomer mixture (GC: two peaks) of ethyl 3,3,5-trimethyl-cyclohexylacetate, this mixture being used directly in the saponification described hereinafter.

Ethyl 3,5-dimethyl-cyclohexylacetate

To a 1 liter autoclave which is fitted with heating means, cooling means and a stirrer are added 54 g of ethyl 3,5-dimethyl-cyclohexylideneacetate, 200 ml of absolute methanol and 3 g of Raney-nickel, which has been washed three times with absolute methanol. The mixture is hydrogenated at 100° C. under a hydrogen pressure of 40 atmospheres. The hydrogen uptake stops after 8 hours. The catalyst is filtered off, the filtrate is concentrated and the residue is distilled. There are obtained 52.3 g of ethyl 3,5-dimethyl-cyclohexylacetate.

B.p.: 56° C./0.7 mm Hg; $n_D^{20} = 1.4440$. Yield: 98%.

Ethyl 3,4-dimethyl-cyclohexylacetate

The analogous hydrogenation of ethyl 3,4-dimethyl-cyclohexylideneacetate yields ethyl 3,4-dimethyl-cyclohexylacetate.

B.p.: 103° C./7 mm Hg; $n_D^{20} = 1.4482$.

Ethyl 2-sec.butyl-cyclohexylacetate

The analogous hydrogenation of ethyl 2-sec.butyl-cyclohexylideneacetate gives ethyl 2-sec.butyl-cyclohexylacetate.

B.p.: 88° C./0.4 mm Hg; $n_D^{20} = 1.4590$.

3,3,5-Trimethyl-cyclohexylacetic acid 875 g of ethyl 3,3,5-trimethyl-cyclohexylacetate are treated in 2.2 l of water with 670 g of 30% sodium hydroxide and the mixture is held at reflux temperature for 2½ hours while stirring. After cooling, the mixture is neutralized, acidified with 420 g of 63% sulphuric acid and extracted with cyclohexane. The cyclohexane extract is washed neutral, evaporated and the 770 g of crude product are distilled. There are obtained 630 g of 3,3,5-trimethyl-cyclohexylacetic acid. (Yield: 82%).

$n_D^{20} = 1.4622$.

3,3,5-Trimethyl-(1 or 6)-(cyclohexenyl or cyclohexylidene)acetic acid

By analogous saponification of ethyl 3,3,5-trimethyl-(1 or 6)-(cyclohexenyl or cyclohexylidene)acetate there is obtained in a yield of 90% 3,3,5-trimethyl-(1 or 6)-(cyclohexenyl or cyclohexylidene)acetic acid.

M.p.: 80°-82° C.

3,5-Dimethyl-cyclohexylacetic acid 44.7 g of ethyl 3,5-dimethyl-cyclohexylacetate are treated with 300 ml of methanol and 15 g of potassium hydroxide, dissolved in 140 ml of water, and saponified by heating to reflux temperature for 3 hours. The working-up yields 35.6 g of a solid crude product which is used directly. A sample is distilled for the purpose of analysis.

B.p.: 120° C./7 mm Hg. Crude yield: 93%.

3,4-Dimethyl-cyclohexylacetic acid

The corresponding saponification of ethyl 3,4-dimethyl-cyclohexylacetate yields 3,4-dimethyl-cyclohexylacetic acid as a liquid crude product.

B.p.: 152° C./7 mm Hg.

2-Sec. butyl-cyclohexylacetic acid

The analogous saponification of ethyl 2-sec. butyl-cyclohexylacetate yields 2-sec. butyl-cyclohexylacetic acid as a liquid crude product.
B.p.: 160° C./0.3 mm Hg.

1-Methyl-2-methylene-3-(prop-1-en-2-yl)-cyclopentane-1-carboxylic acid.

75 ml of dry tetrahydrofuran and 23 g of magnesium shavings are added to a round flask which is fitted with a stirrer, thermometer, dropping funnel and reflux condenser. Without stirring there is added thereto slowly (within 4 hours) a solution of 112.4 g of 1-methyl-2-chloromethyl-3-(prop-1-en-2-yl)-cyclopent-1-ene in 100 ml of tetrahydrofuran. The mixture is brought to 60°–65° for 1 hour and then cooled to $-10°$. A carbon dioxide stream is conducted through the solution, which is cooled to $-10°$ C. The amount of carbon dioxide introduced is weighed; it amounts to 29.5 g. The mixture is left to stand at room temperature overnight. The mixture is then cooled to 10° C. and decomposed with 300 ml of a 10% hydrochloric acid solution. The acid solution is extracted with ether, the organic acid formed is taken up as the sodium salt (treatment with 10% sodium hydroxide) from the ether into the aqueous phase, which is washed with ether. After acidifying with 10% orthophosphoric acid, the mixture is extracted with ether and the etherial solution is dried over sodium sulphate. The solvent is evaporated and there are obtained 78.2 g (yield: 66%) of crude 3-isopropenyl-2-methylene-1-methyl-cyclopentanecarboxylic acid, which are recrystallized with hexane.
M.p.: 66.5°–68° C.

3,3,5-Trimethyl-cyclohexylacetyl chloride 114 g of 3,3,5-trimethyl-cyclohexylacetic acid in 350 ml of dry ether in a round flask which is fitted with a thermometer, stirrer, reflux condenser and dropping funnel are treated rapidly with 32.8 g of phosphorus trichloride and the mixture is subsequently held at reflux temperature for a further 4 hours. The phosphorous acid is decanted off and the ether is evaporated in vacuo. There are obtained 128 g (yield: quantitive) of crude 3,3,5-trimethyl-cyclohexylacetyl chloride.

3,3,5-Trimethyl-(1 or 6)-(cyclohexenyl or cyclohexylidene)acetyl chloride

This acid chloride is obtained by the analogous treatment of 3,3,5-trimethyl-(1or 6)-(cyclohexenyl or cyclohexylidene)acetic acid. Yield after distillation: 52%.
$n_D^{20} = 1.4750$.

1-Methyl-2-methylene-3-(prop-1-en-2-yl)-cyclopentane-1-carboxylic acid chloride This acid chloride is obtained by the analogous treatment of 1-methyl-2-methylene-3-(prop-1-en-2-yl)-cyclopentane-1-carboxylic acid. Yield after distillation: 51%.
$n_D^{20} = 1.4930$.

3,5-Dimethyl-cyclohexylacetyl chloride

This starting material is obtained by the analogous treatment of 3,5-dimethyl-cyclohexylacetic acid.
B.p.: 73° C./1.5 mm Hg; $n_D^{20} = 1.4603$.

3,4-Dimethyl-cyclohexylacetyl chloride

This starting material is obtained by the analogous treatment of 3,4-dimethyl-cyclohexylacetic acid.
B.p.: 68° C./0.35 mm Hg; $n_D^{20} = 1.4692$.

2-Sec.butyl-cyclohexylacetyl chloride

This starting material is obtained by the analogous treatment of 2-sec.butyl-cyclohexylacetate.
B.p.: 71° C./0.12 mm Hg; $n_D^{20} = 1.4800$.

EXAMPLE 2

2-(3,3,5-Trimethyl-cyclohexylacetyl)-cyclopentanone 111 g of freshly distilled morpholinocyclopentene, 71.7 g of triethylamine and 900 ml of chloroform are added to a round flask which is fitted with a thermometer, stirrer, reflux condenser and dropping funnel and the mixture is cooled to 0° C. Under a nitrogen atmosphere there are slowly added dropwise thereto 128 g of crude 3,3,5-trimethyl-cyclohexylacetyl chloride in 200 ml of chloroform. The flask content is stirred until it has reached a temperature of 20° C. and it is then warmed at 40° C. for a further 7 hours. After 12 hours, 76.2 of concentrated hydrochloric acid in 190 ml of water are added thereto and the flask content is held at reflux temperature for 2½ hours. Thereafter, the organic phase is separated, the aqueous phase is extracted twice with chloroform and the combined chloroform extracts are washed as follows: three times with 10% hydrochloric acid, once with water, once with bicarbonate solution and finally with sodium chloride solution until neutral. Now it is concentrated in a rotary evaporator and the crude product (212 g) is distilled in vacuo. There are obtained 90 g (yield: 58%) of 2-(3,3,5-trimethylcyclohexylacetyl)-cyclopentanone.
B.p.: 111.5° C./0.25 mm Hg.
Odour: intensively woody, animal-like; extremely diffusive, excellent tenacity.

2-[3,3,5-Trimethyl-(1 or 6)-(cyclohexenyl or cyclohexylidene)acetyl]-cyclopentanone If the foregoing conditions are used on distilled 3,3,5-trimethyl-(1 or 6)-(cyclohexenyl or cyclohexylidene)acetyl chloride, then there is obtained 2-[3,3,5-trimethyl-(1 or 6)-(cyclohexenyl or cyclohexylidene)acetyl]-cyclopentanone in a yield of 62%.
B.p.: 103° C./0.08 mm Hg.
Odour: woody, animal-like; very diffusive.

2-[1-Methyl-2-methylene-3-(prop-1-en-2-yl)-cyclopentylcarbonyl]-cyclopentanone The same treatment of distilled 1-methyl-2-methylene-3-(prop-1-en-2-yl)-cyclopentane-1-carboxylic acid chloride give in 36.5% yield 2-[1-methyl-2-methylene-3-(prop-1-en-2-yl)-cyclopentylcarbonyl]-cyclopentanone.
B.p.: 119° C./0.58 mm Hg.
Odour: strongly woody, cedarous.

2-(3,5-Dimethyl-cyclohexylacetyl)-cyclopentanone

If 3,5-dimethyl-cyclohexylacetyl chloride is subjected to the treatment described earlier, then there is obtained 2-(3,5-dimethylcyclohexylacetyl)-cyclopentanone.
B.p.: 129° C./0.1 mm Hg; $n_D^{20} = 1.4950$.
Odour: intensively woody and animal-like; diffusive, good tenacity.

2-(3,4-Dimethyl-cyclohexylacetyl)-cyclopentanone

By subjecting 3,4-dimethyl-cyclohexylacetyl chloride to the procedure described earlier there is obtained 2-(3,4-dimethyl-cyclohexylacetyl)-cyclopentanone.

B.p.: 133° C./0.8 mm Hg; $n_D^{20}=1.5080$.

Odour: intensively woody animal-like with a minty note, diffusive, good tenacity.

2-(2-Sec.butyl-cyclohexylacetyl)-cyclopentanone

By treating 2-sec.butyl-cyclohexylacetyl chloride in the manner described above there is obtained 2-(2-sec.-butyl-cyclohexylacetyl)-cyclopentanone.

B.p.: 137° C./0.28 mm Hg; $n_D^{20}=1.5117$.

2-(1,2-Dimethyl-3-isopropyl-cyclopentylcarbonyl)-cyclopentanone 9.6 g of 2-[1-methyl-2-methylene-3-(prop-1-en-2-yl)-cyclopentylcarbonyl]-cyclopentanone are treated in 100 ml of absolute alcohol with 1 g of 5% palladium-on-carbon and the mixture is hydrogenated at normal pressure. After completion of the hydrogen uptake (8 hours), the mixture is filtered, the filtrate is concentrated and the residue is chromatographed on a hundred-fold amount of silica gel with toluene/ethyl acetate (1:2). There are obtained 1.7 g of 2-(1,2-dimethyl-3-isopropyl-cyclopentylcarbonyl)-cyclopentanone, which are contaminated with a small amount (<5%) of 2-(1,2-dimethyl-3-isopropyl-cyclopent-2-en-1-yl-carbonyl)-cyclopentanone or 2-(1,2-dimethyl-3-isopropylidenecyclopentyl carbonyl)-cyclopentanone. $n_D^{20}=1.5042$.

Odour: intensively woody, diffusive, good tenacity.

In the following Examples "compound Ia", "compound Ib" and "compound Ic" have the following significances:

"Compound Ia": 2-(3,3,5-trimethyl-cyclohexylacetyl)-cyclopentanone.

"Compound Ib": 2-(3,5-dimethyl-cyclohexylacetyl)-cyclopentanone.

"Compound Ic": 2-(3,4-dimethyl-cyclohexylacetyl)-cyclopentanone.

EXAMPLE 3

(a) Perfume base in the direction of fougère

|  | Parts by weight |
|---|---|
| Lavandin oil | 140 |
| Geranium oil (African) | 140 |
| Coumarin | 140 |
| Benzoin resinoid (Siam) | 140 |
| Tree moss absolute (aloresine) | 60 |
| Patchouli oil | 60 |
| Bergamotte oil | 60 |
| Vetiver oil (Bourbon) | 40 |
| Musk ketone | 60 |
| Musk xylene | 60 |
|  | 900 |
| Compound Ia | 100 |
|  | 1000 |

By adding 10% of the compound Ia the coumarin note, which predominates in the fougère base, is suppressed. At the same time, the composition becomes lighter and fresher. The lavender notes are emphasized in a desirable manner.

(b) Spicy base

|  | Parts by weight |
|---|---|
| Benzyl acetate | 100 |
| Hydroxycitronellal | 100 |
| Phenylethyl alcohol | 100 |
| Amyl acetate | 100 |
| Patchouli oil | 80 |
| Ylang oil | 50 |
| Eugenol | 50 |
| Linalyl acetate | 60 |
| Musk ketone | 50 |
| Cedryl acetate | 30 |
| Epoxycedrene | 30 |
| Vertofix coeur TM (acetylcedrene) | 30 |
| Coumarin | 30 |
| Spearmint oil | 15 |
| Thyme oil | 15 |
| Methyl salicylate | 5 |
| Lemon oil | 5 |
| Dipropyleneglycol (DPG) | 100 |
|  | 950 |
| Compound Ia | 50 |
|  | 1000 |

The addition of 5% of compound Ia produces not only an intensification of the olfactory intensity, but also an improvement in the olfactory quality of the spicy base. The olfactory complex clearly receives more volume.

(c) Perfume base in the direction of wood

|  | Parts by weight |
|---|---|
| Madrox TM Givaudan (1-methyl-1-methoxy-cyclododecane) | 150 |
| Vetivenyl acetate | 150 |
| Sandela ® Givaudan [3-isocamphyl-(5)-cyclohexanol] | 150 |
| Linalool | 100 |
| Patchouli oil | 50 |
| Ironal ® Givaudan (6-methyl-α-ionone) | 50 |
| Linalyl acetate | 50 |
| Citronellol | 50 |
| Benzyl acetate | 30 |
| Tree moss colourless absolute | 30 |
| α-Amylcinnamaldehyde | 20 |
| Methylnonylacetaldehyde (10% in DPG) | 20 |
| Eugenol | 20 |
| C-11-aldehyde (10% in DPG) | 10 |
| Ciste oil French (labdanum) | 10 |
| Sandalore ® Givaudan (3-methyl-5-(2,2,3)-trimethylcyclopent-3-en-1-yl)pentan-2-ol | 10 |
|  | 900 |
| Compound Ia | 100 |
|  | 1000 |

By adding 10% of compound Ia the olfactory intensity of the woody base is increased in a significant manner. The patchouli notes are modified in an advantageous manner in the direction of cedar, leather and animal-like notes.

(d) Perfume base in the direction of chypre

|  | Parts by weight |
|---|---|
| α-Ionone | 200 |
| Musk ambrette | 100 |
| Phenylethyl alcohol | 30 |
| Bergamotte oil | 70 |
| Vertofix coeur | 50 |
| Jasmine (synthetic) | 40 |
| Patchouli oil | 40 |
| Rhodinol | 30 |

|  | Parts by weight |
|---|---|
| Clove base | 30 |
| α-Hexylcinnamaldehyde | 30 |
| Civet oil (10% in DPG) | 20 |
| Sandalore ® Givaudan | 10 |
| Artemisia essence (mugwort oil) | 10 |
| C-11-aldehyde (10% in DPG) | 10 |
| Tree moss absolute | 50 |
| Styrallyl acetate | 20 |
| DPG | 200 |
|  | 990 |
| Compound Ia | 10 |
|  | 1000 |

The addition of only 1% of compound Ia to this chypre base already produces an olfactory intensification. At the same time, the woody notes are emphasized and the cedar character is accentuated.

(e) Animal-like base

|  | Parts by weight |
|---|---|
| Sandela ® Givaudan | 100 |
| Madrox ™ Givaudan | 100 |
| Vertofix coeur ™ | 100 |
| Patchouli oil | 50 |
| Benzyl salicylate | 40 |
| Linalyl acetate | 40 |
| Myrrh oil | 30 |
| Benzoin resinoid (Siam) | 30 |
| Ethylene brassylate | 30 |
| Castoreum (synthetic) | 30 |
| C-11-aldehyde (10% in DPG) | 20 |
| C-12-aldehyde L (10% in DPG) | 20 |
| β-Ionone | 20 |
| p-Cresyl-phenylacetate | 5 |
| Indole | 5 |
| DPG | 330 |
|  | 950 |
| Compound Ia | 50 |
|  | 1000 |

The addition of 5% of compound Ia clearly confers to this composition more character and accentuates the castoreum and leather notes.

(f) Spicy perfume base

|  | Parts by weight |
|---|---|
| Bergamotte oil | 200 |
| Patchouli oil | 200 |
| Sandalwood oil | 200 |
| Myrascone ™ Givaudan | 100 |
| Methyl dihydrojasmonate | 70 |
| α-Ionone | 50 |
| p.Tert.butyl-cyclohexanol acetate | 50 |
| Basil oil | 30 |
|  | 900 |
| Compound Ia | 100 |
|  | 1000 |

By adding 10% of compound Ia this olfactory complex becomes more aromatic and more spicy. It receives more "volume" and, at the same time, becomes more harmonic and rounded-off.

(g) Perfumery base in the direction of chypre

|  | Parts by weight |
|---|---|
| Hydroxycitronellal | 100 |
| Bergamotte oil | 80 |
| Methyl dihydrojasmonate | 80 |
| α-Hexylcinnamaldehyde | 80 |
| Phenylethyl alcohol | 80 |
| Tree moss absolute (colourless) | 40 |
| Patchouli oil | 40 |
| Linalool | 40 |
| α-Ionone | 40 |
| Musk ketone | 40 |
| Vetiver oil | 20 |
| Sandalwood oil | 20 |
| Benzyl acetate | 20 |
| Styrallyl acetate | 5 |
| Undecalactone | 5 |
| C-11-aldehyde (10% in DPG) | 5 |
| Civet oil (10% in DPG) | 5 |
| Dipropyleneglycol | 200 |
|  | 900 |
| Compound Ib | 100 |
|  | 1000 |

By adding 10% of the compound Ib the base receives a woody-cedarous note which usually can only be achieved by adding cedarwood oil. At the same time, the base becomes much more powerful, tangy, fresher and also drier. From the former feminine basic composition there is produced a base which is very well suited for mens colognes.

(h) Perfumery base in the direction of tea

|  | Parts by weight |
|---|---|
| Bergamotte oil | 150 |
| Linalool | 100 |
| Hydroxycitronellal | 100 |
| Methyl dihydrojasmonate | 60 |
| Patchouli oil | 40 |
| Basil oil | 30 |
| Methyleugenol | 20 |
| β-Ionone | 20 |
| Formiate oxyoctaline (3,4,5,6,7,8,9,10-octahydro-1,2,8,10-tetramethyl-5-formoxy-naphthalene) | 10 |
| Galaxolide ® (1,3,4,6,7,8-hexahydro-4,6,6,7,8,8-hexamethyl-cyclopenta-γ-2-benzopyran)IFF | 10 |
| Bornyl acetate | 10 |
| 2,2,8-Trimethyl-7-nonen-3-ol | 10 |
| Tree moss absolute (colourless) | 10 |
| Lemon oil | 10 |
| Vertofix ™ | 10 |
| Indole (10% in dipropyleneglycol) | 10 |
| Dipropyleneglycol | 350 |
|  | 950 |
| Compound Ic | 50 |
|  | 1000 |

By adding 5% of the compound Ic the original base becomes much softer and powdery. Moreover, it now becomes flowery and pleasantly tangy, herby, and spicy.

We claim:

1. A compound of the formula

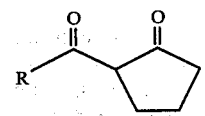

wherein R signifies an aliphatic group of the formula

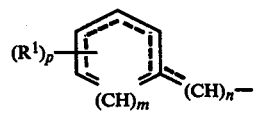

in which $R^1$ is $C_{1-4}$alkyl, $C_{1-4}$-alkylidene or $C_{2-4}$-alkenyl and the sum of the carbon atoms in these groups is 2–5, m and n are 0 or 1, p is 1, 2 or 3 and the dotted lines represent one or two optional double bonds, with the exception of 2-[3,3,5-trimethylcyclohexylacetyl]-cyclopentanone.

2. A compound according to claim 1 wherein R is

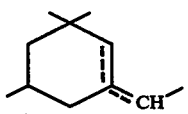

3. A compound according to claim 1 wherein R is

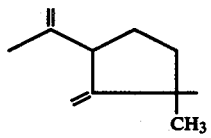

and named 2-[1-Methyl-2-methylene-3-(prop-1-en-2-yl)-cyclopentylcarbonyl]-cyclopentanone.

4. A compound according to claim 1 wherein R is

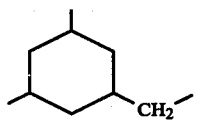

and named 2-(3,5-Dimethyl-cyclohexylacetyl)-cyclopentanone.

5. A compound according to claim 1 wherein R is

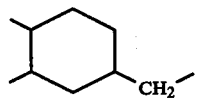

and named 2-(3,4-Dimethyl-cyclohexylacetyl)-cyclopentanone.

6. A compound according to claim 1 wherein R is

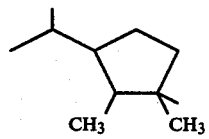

and named 2-(1,2-Dimethyl-3-isopropyl-cyclopentylcarbonyl)-cyclopentanone.

7. A compound according to claim 1 wherein R is

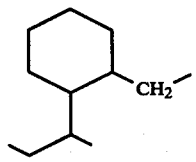

and named 2-(2-Sec.butyl-cyclohexylacetyl)-cyclopentanone.

8. Odorant compositions containing an olfactorily effective amount of a compound of the formula

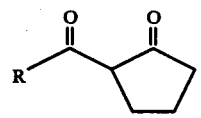

(I)

wherein R signifies an aliphatic group of the formula

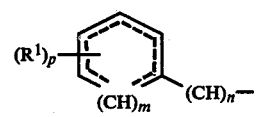

in which $R^1$ is $C_{1-4}$-alkyl, $C_{1-4}$-alkylidene or $C_{2-4}$-alkenyl and the sum of the carbon atoms in these groups is 2–5, m and n are 0 or 1, p is 1, 2 or 3 and the dotted lines represent one or two optional double bonds and at least one other odorant.

9. An odorant composition according to claim 8 containing 2-(3,3,5-trimethylcyclohexylacetyl)-cyclopentanone.

10. An odorant composition according to claim 8 wherein R is

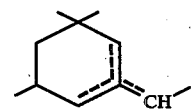

11. An odorant composition according to claim 8 containing 2-[1-methyl-2-methylene-3-(prop-1-en-2-yl)-cyclopentylcarbonyl]cyclopentanone.

* * * * *